(12) United States Patent
Kishioka

(10) Patent No.: US 7,471,380 B2
(45) Date of Patent: Dec. 30, 2008

(54) RUBBING ANGLE-MEASURING EQUIPMENT, AND MANUFACTURING METHODS OF LIQUID CRYSTAL DISPLAY DEVICE AND OPTICAL FILM

(75) Inventor: Atsushi Kishioka, Fujisawa (JP)

(73) Assignee: Hitachi Displays, Ltd., Mobara-shi (JP)

( * ) Notice: Subject to any disclaimer, the term of this patent is extended or adjusted under 35 U.S.C. 154(b) by 117 days.

(21) Appl. No.: 11/693,755

(22) Filed: Mar. 30, 2007

(65) Prior Publication Data
US 2007/0236686 A1 Oct. 11, 2007

(30) Foreign Application Priority Data
Apr. 7, 2006 (JP) ............... 2006-105822

(51) Int. Cl.
*G01B 11/26* (2006.01)
(52) U.S. Cl. ...................... 356/138; 349/191
(58) Field of Classification Search ............. 356/138; 382/141; 349/187, 191
See application file for complete search history.

(56) References Cited
U.S. PATENT DOCUMENTS
5,394,245 A * 2/1995 Sato .......................... 356/369
6,831,722 B2 * 12/2004 Ishikawa et al. ............ 349/117
2003/0011732 A1 * 1/2003 Ishihara et al. ............. 349/117

FOREIGN PATENT DOCUMENTS
JP 06-059230 3/1994

\* cited by examiner

Primary Examiner—Roy M Punnoose
(74) Attorney, Agent, or Firm—Antonelli, Terry, Stout & Kraus, LLP.

(57) ABSTRACT

A rubbing angle measuring equipment of the invention includes an light source unit, a measuring optical system, an imaging means, and an image evaluation means in which the measuring optical system is adapted such that a light from the light source unit passes by way of an illumination optical system and a polarizer to a rubbed measuring object and further passes by way of an analyzer and a focusing optical system to the imaging means, and the surface of the measuring object is focused to the imaging means, and in which image signals obtained by the imaging means are transmitted to the image evaluation means where signals having an intense periodicity in the image are detected, to measure the rubbing angle of the measuring object in a nondestructive manner, within a short period and at a high accuracy of 0.1° or more.

15 Claims, 12 Drawing Sheets

FIG.1
(a)
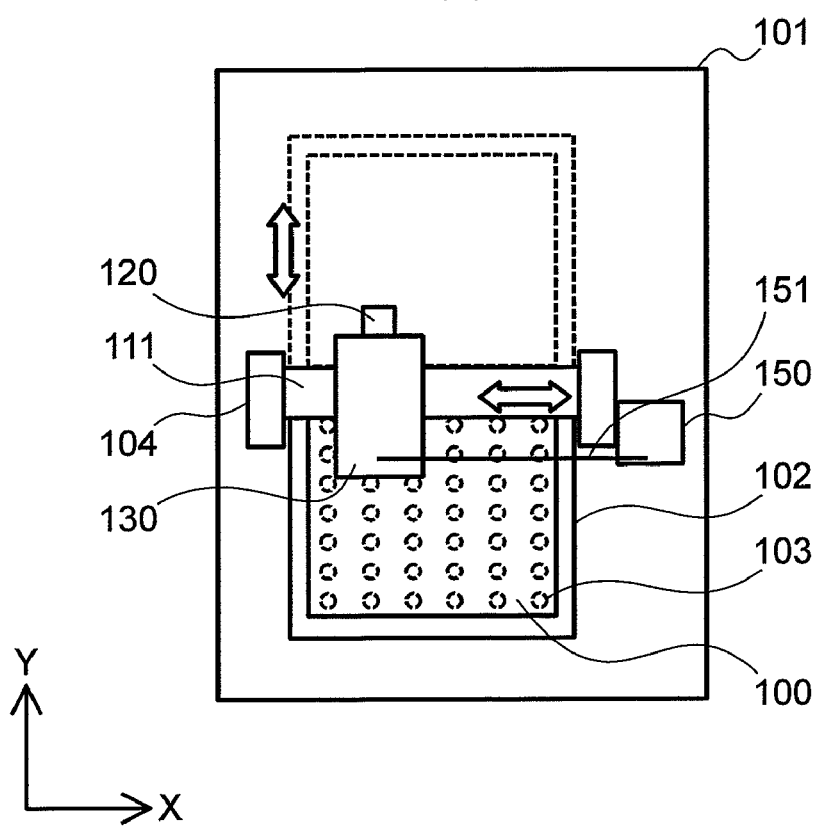
(b)
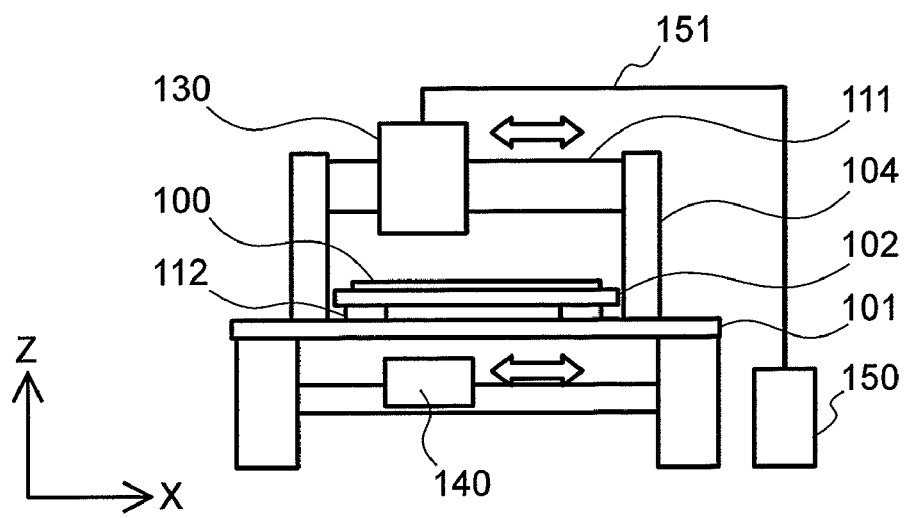

FIG.5
(a)
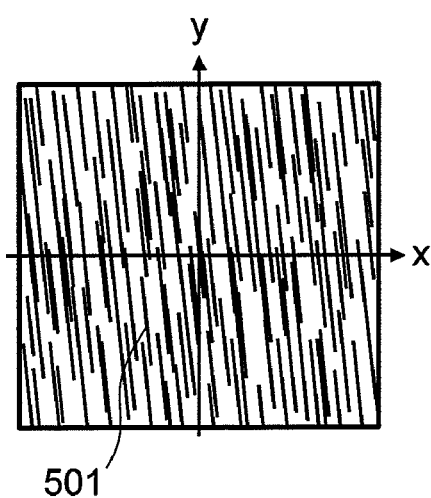
501
(b)
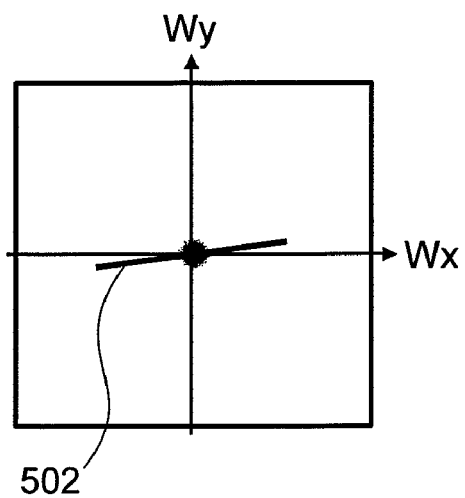
502
(c)
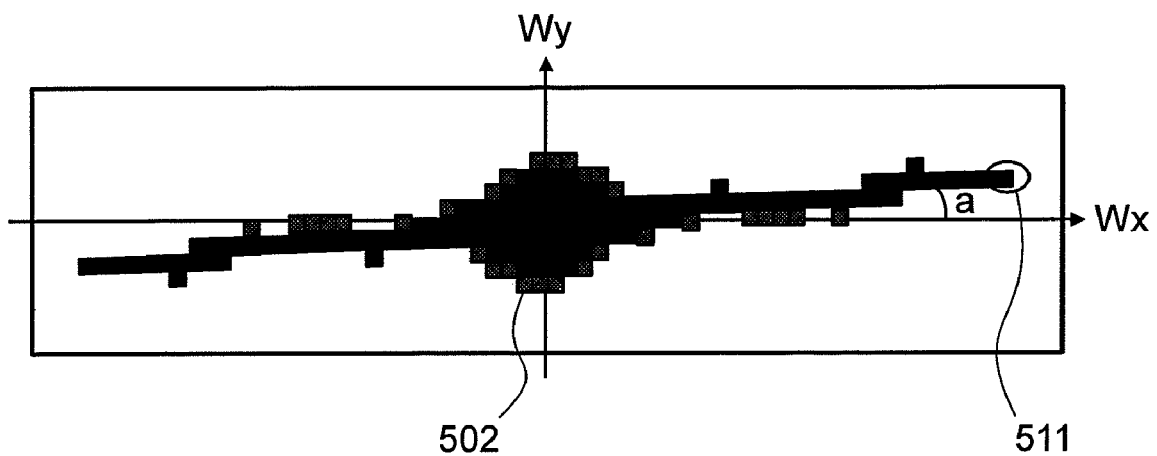
502　　511

FIG.6
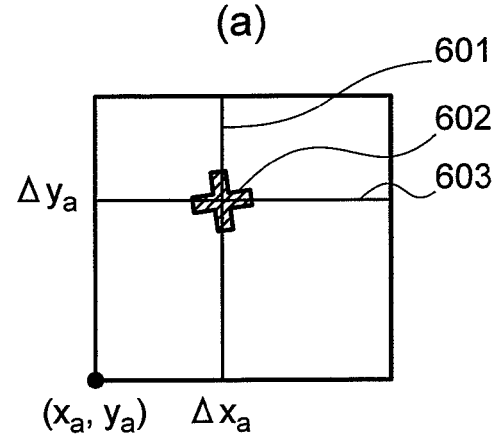
(a)
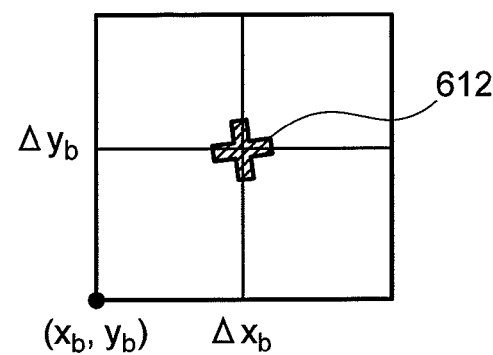
(b)
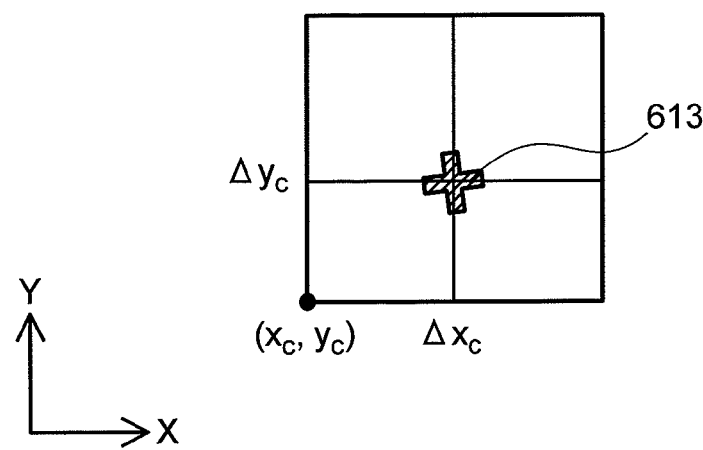
(c)

FIG.9
(a)
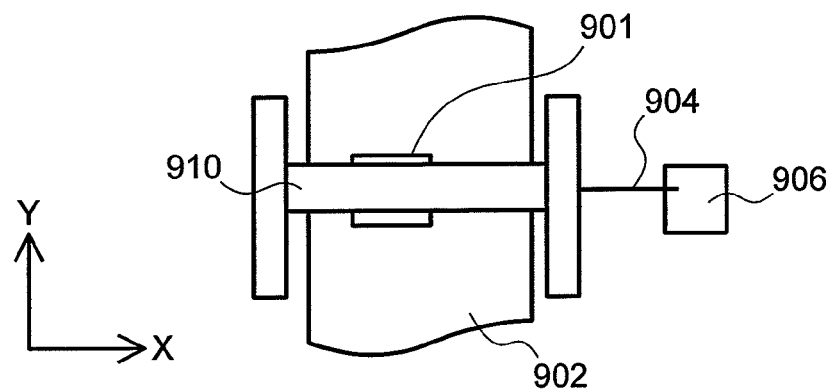
(b)
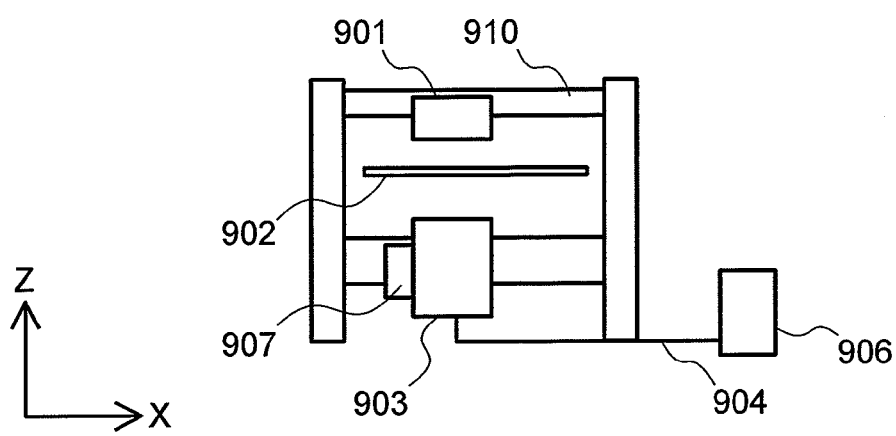
(c)
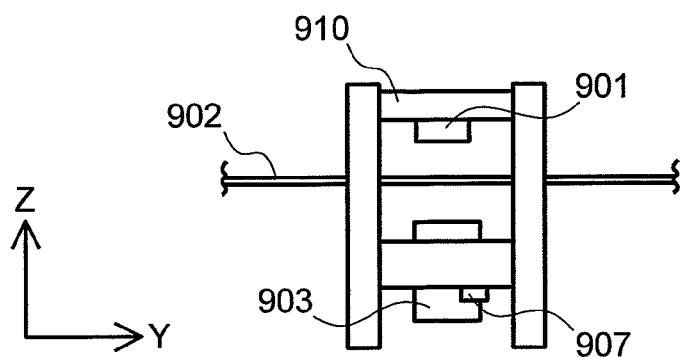

FIG.15
(a)
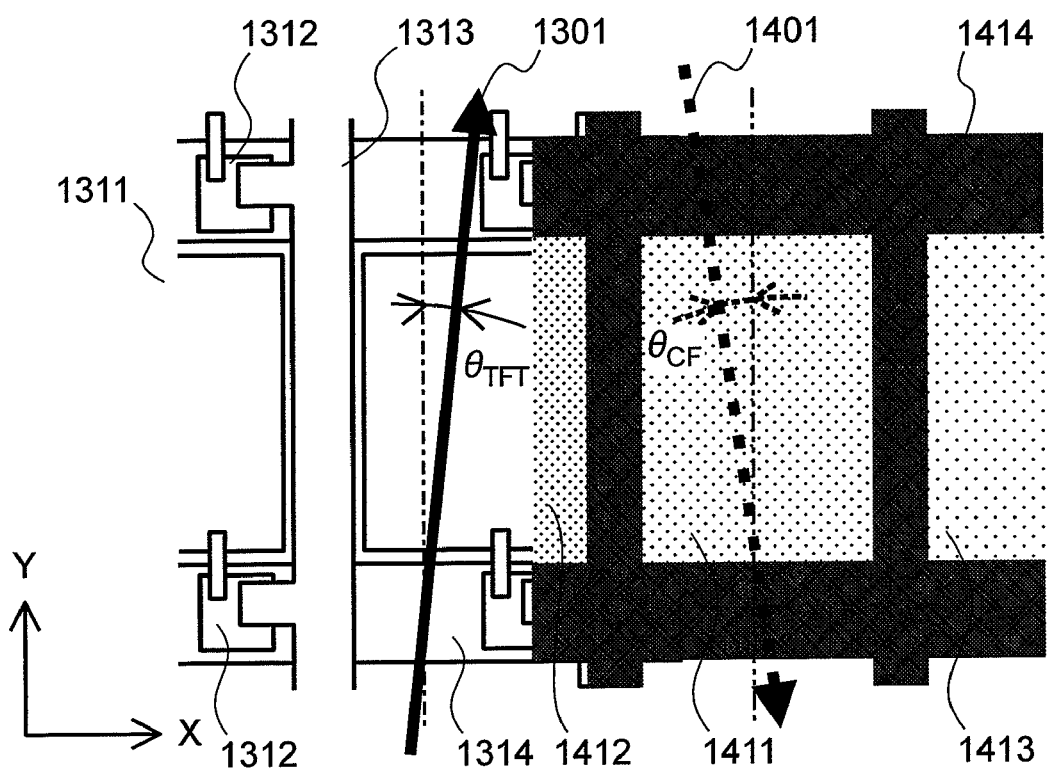
(b)
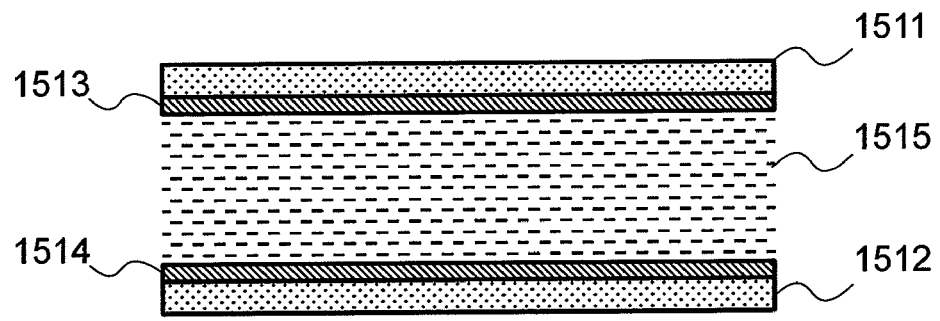

RUBBING ANGLE-MEASURING EQUIPMENT, AND MANUFACTURING METHODS OF LIQUID CRYSTAL DISPLAY DEVICE AND OPTICAL FILM

The present application claims priority from Japanese application JP2006-105822 filed on Apr. 7, 2006, the content of which is hereby incorporated by reference into this application.

BACKGROUND OF THE INVENTION

1. Field of the Invention

The present invention concerns an apparatus for nondestructive measurement of a rubbing angle (alignment control direction) in a substrate just after a rubbing treatment of the substrate, as well as manufacturing methods of a liquid crystal display device and an optical film using a substrate controlled for the rubbing angle by the measurement.

2. Description of the Related Art

FIG. 12 schematically shows the structure of an IPS (in-plane switching) type liquid crystal display device as an example of a liquid display device. An unpolarized light emitted from a backlight 1241 passes through a lower polarizer plate 1231 and is polarized. The polarized light passes a liquid crystal panel 1211 and, further, passes an upper polarizer plate 1212, by which a liquid crystal device displays an image. Between the polarizer plate and the liquid crystal panel, a retardation plate is sometimes provided for color compensation to the liquid crystal panel 1211 (bifringence thereof) or for improving optical characteristics such as a view angle characteristic. FIG. 12 shows the structure of a liquid crystal display device using a composite film 1211 formed by stacking a retardation plate 1213 to the upper polarizer plate 1212. A composite film 1211 has a polarization axis 1214 of the polarizer plate 1212 and a slow axis (phase retardation axis) 1215 of the phase retardation plate 1213.

The upper polarizer plate 1212 and the lower polarizer plate 1231 are bonded on both surfaces of the liquid crystal panel 1221 (respective main surfaces of a first glass substrate 1223 and a second glass substrate 1224) such that the polarization axis 1214 of the upper polarizer plate 1212 and the polarization axis 1232 of the lower polarizer plate 1231 are crossed at 90° (to constitute Crossed Nicols). The amount of light transmitting the upper polarizer plate 1212 is controlled by controlling liquid crystals 1222 of the liquid crystal panel 1221 thereby changing the polarization direction of the light passing the liquid crystal panel 1221. A so-called inverse parallel rubbing treatment of moving rubbing rollers to the directions opposite to each other along an illustrated rubbing direction 1225 is applied to respective main surfaces of the first glass substrate 1223 and the second glass substrate 1224 in contact with the liquid crystals 1222. In a period where an electric field is not applied to the liquid crystals 1222 (hereinafter referred to as a non-electric field period), the liquid crystals 1222 are arranged in accordance with the direction of an anchoring energy applied by rubbing to the substrates (substantially equal with the rubbing direction 1225). The direction of the anchoring energy is referred to as an alignment axis. An IPS liquid panel is constructed such that the alignment axis is at 0° or 90° relative to the polarization axis 1232 of the lower polarizer plate 1231. In an initial state where the electric field is not applied to the liquid crystals 1222, since the light incident from the lower polarizer plate (backlight 1241) to the liquid crystal panel 1221 is not changed for the polarization direction thereof by the liquid crystals 1222, it is interrupted by the upper polarization plate 1212 having the polarization axis 1214 crossing the polarization direction and a screen of the liquid crystal display device is displayed black. When the polarization direction of a light passing the liquid crystal panel 1221 changes by applying an electric field to the liquid crystal panel 1221 to change the alignment direction of the liquid crystals 1222, and the amount of a light transmitting the upper polarizer plate 1212 increases and the screen of the liquid crystal display device is displayed white. In the liquid crystal display, the amount of light is changed by the switching of the liquid crystals by the electric field as described above.

A relation between the anchoring energy and the twisting of liquid crystals (which changes the aforementioned alignment direction) in the liquid crystal panel is to be described with reference to FIG. 13 to FIG. 15. In the following description, one of the pair of substrate 1223 and 1224 sandwiching the liquid crystals 1222 described above is referred to as a TFT substrate in which plural pixels each having a pixel electrode and a thin film transistor (hereinafter referred to as TFT) for controlling the application of an electric field to the liquid crystals are arranged in a 2-dimensional manner, and the other of them is referred to as a CF substrate in which a color filter (hereinafter referred to as CF) is formed for providing a specific color to a light passing liquid crystals. FIG. 13 shows, in an enlarged scale, a region formed with one of the plural pixels on the main surface of the TFT substrate and FIG. 14 shows, in an enlarged scale, a region of a main surface of the CF substrate opposed by way of a liquid crystal layer to the region of the main surface of the TFT substrate. FIG. 13 shows the pixel electrode (for example, an ITO interconnection (an ITO wiring or an ITO layer) formed of indium-tin oxide) 1311, a thin film transistor 1312 for controlling the potential thereof, a drain interconnection (also described as, a drain wiring, or a drain line) 1313 for supplying an image signal to the thin film transistor 1312, a gate interconnection (also described as, a gate wiring, or a gate line) 1314 for controlling the supply of the image signal from the thin film transistor 1312 to the pixel electrode 1311, and a source interconnection (also described as, a source wiring, or a source line) 1315 for electrically connecting the thin film transistor 1312 and the pixel electrode 1311. The TFT substrate is also referred to as an array circuit substrate in view of the arrangement of TFTs for applying a voltage to the liquid crystals on every pixel on the main surface. FIG. 14 shows a color filter 1411, opposed to the pixel electrode 1311, a pair of color filters 1412 and 1413 adjacent on both sides of the color filter 1411, and a black matrix 1414 spacing adjacent color filters. Colors of the color filters 1411, 1412, and 1413 are different from each other and the color filters are formed, for example, with a G (green) color resist for the color filter 1411, an R (red) color resist for the color filter 1412, and a B (blue) for resist for the color filter 1413, respectively.

The main surface of the TFT substrate shown in FIG. 13 is rubbed along direction 1301 deviated from an interconnection direction (shown by a dashed-dotted line) at an angle of $\theta_{TFT}$, and the main surface of the CF substrate (color filter substrate) shown in FIG. 14 is rubbed along direction 1401 deviated from the interconnection direction (shown by a dashed-dotted line) at an angle of $\theta_{CF}$. The interconnection direction illustrated herein is defined as an extending direction of the drain interconnection 1313 at the main surface of the TFT substrate and, as the extending direction of the drain interconnection 1313 of the TFT substrate is projected to the main surface of the CF substrate at the main surface of the CF substrate. An alignment film is coated to the main surface of the TFT substrate and the main surface of the CF substrate before the rubbing treatment, and the anchoring energy is given to each of the alignment films by the rubbing treatment. Then, the TFT substrate and the CF substrate are overlapped to each other such that the rubbing directions 1301 and 1401 applied respectively to them are in inverse parallel, and liquid crystals are injected in a space separating the main surface of the TFT substrate and the main surface of the TFT substrate to prepare a panel shown in FIG. 15(*a*). FIG. 15(*a*) shows a portion of the TFT substrate and the CF substrate in which the respective main surfaces are rubbed in the directions 1301 and 1401 and the CF substrate is partially cut away such that the structure of the main surface of the TFT substrate covered with the CF substrate can be observed. Further, FIG. 15(*b*) shows a cross section of the panel shown in FIG. 15(*a*). As shown in FIG. 15(*b*), an alignment film 1513 is formed to the main surface of a CF substrate 1511, and an alignment film 1514 is formed to the main surface of a TFT substrate 1512 and liquid crystals 1515 are sealed between the main surfaces.

In the panel comprising the substrate rubbed in the direction deviated from the direction of axis Y in an orthogonal coordinate (that is, the interconnection direction) by a predetermined angle in FIG. 15(*a*), liquid crystals near the main surface of the TFT substrate are arranged along the anchoring energy applied to the alignment film 1514 on the side of the TFT substrate 1512, while the liquid crystals near the main surface of the CF substrate are arranged along the anchoring energy applied to the alignment film 1513 on the side of the CF substrate 1511. Liquid crystals 1515 present between them are arranged being twisted so as to connect the anchoring energy of the upper and lower substrates (CF substrate 1511, TFT substrate 1512). In the liquid crystal panel, since the optical characteristic such as contrast is lowered when the alignment angle of the liquid crystals is deviated relative to the polarization axis, it is important to apply rubbing at an angle as a designed value (being aligned with the axis Y in this case).

Further, as shown in FIG. 12, the liquid crystal display has optical films such as the polarization film 1212 and the retardation film 1213 and each of the optical films has an optical anisotropic axis. Upon manufacturing the optical film or bonding it to the liquid crystal panel, in a case where the angle of the optical anisotropic axis is deviated from a designed value thereof, the optical performance of the liquid crystal display is lowered. Accordingly, control for the optical anisotropic axis is important also in the manufacturing of the optical film.

Measurement for the angle of the liquid crystal alignment axis of a liquid crystal panel or an optical film includes, as a general method, a method of measuring refractive index anisotropy (retardation). This is a method of rotating a measuring object (liquid crystal panel or optical film) to a polarization axis under Crossed Nichols thereby measuring an angle at which the transmittance is lowered most. Further, as a method of inspecting a rubbed substrate, JP-A No. Hei 6-59230 discloses a technique of observing a rubbed substrate surface under Crossed Nichols and evaluating the adequacy of rubbing based on the image of streaks thereof.

SUMMARY OF THE INVENTION

In a rubbing process as one of manufacturing processes of a liquid crystal panel or an optical film, even when a fabrication accuracy of a rubbing machine is improved, it is difficult to control the rubbing angle at an accuracy of 0.2° or higher by dispersion of rubbing conditions attributable to a rubbing cloth such as cloth grain. Further, along with enlarging scale of substrates handled in the liquid crystal panel manufacturing process in recent years, in-plane distribution of the rubbing angle due to dispersion of the rubbing cloth has caused a significant problem and the control for the rubbing angle has become an important subject. While the measuring method of utilizing the refractive index anisotropy of liquid crystals enables angle measurement of the liquid crystal alignment axis at high accuracy, the measurement requires formation of a liquid crystal layer (for example, sealing of liquid crystals to a liquid crystal panel). Accordingly, it was difficult to conduct measurement just after rubbing or feed back the result of the measurement instantly to a rubbing process. The present invention intends to measure a rubbing angle at the surface of an alignment film just after rubbing in an nondestructive manner and in a short time at a high accuracy of 0.1° or higher for feeding back to the rubbing process or for feeding forward to processes after the rubbing process in the production line of liquid crystal panels or optical films.

The present invention mainly intends to measure a rubbing angle of an measuring object by using a rubbing angle measurement equipment including a measuring system comprising a light source, an illumination optical system, a polarizer, an analyzer, a focusing optical system and imaging means, and means for detecting the attitude of a measuring object, and imaging the surface of the measuring object after rubbing under Crossed Nichols, and conducting two-dimensional fast fourier transformation processing to an image, or conducting differential processing to an image, thereby detecting a signal having an intense periodicity in the image.

Typical structures and processes of a rubbing angle measuring apparatus and manufacturing methods of a liquid crystal display device and an optical film according to the invention are as described below.

A rubbing angle measuring equipment of structure 1 includes:

a light source unit, a measuring optical system, an imaging means and image evaluation means in which the light source unit is constituted such that a light from a light source is illuminated through an illumination optical system and a polarizer to a surface-rubbed measuring object, the measuring optical system is constituted such that the light transmitting the measuring object is entered through an analyzer and a focusing optical system to the imaging means and focused on the surface of the measuring object, and the image evaluation means receives image signals obtained by the imaging means, detects signals having an intense periodicity in the image and measures the rubbing angle of the measuring object. The surface of the measuring object is applied with the rubbing for aligning the liquid crystals by the treatment. The light source unit, the measuring optical system and the imaging means constitute together with the measuring object an optical system, and the image on the surface of the measuring object obtained by the imaging means is sent electrically to the image evaluation means.

A rubbing angle measuring equipment of structure 2 according to the structure 1 of the rubbing angle measuring equipment, wherein the image evaluation means detects signals having the intense periodicity in the image on the surface of the measuring object by a two-dimensional fast fourier transforming processing of the image signals.

A rubbing angle measuring equipment of a structure 3 according to the structure 1 of the rubbing angle measuring equipment, wherein the image evaluation means detects the signals having the intense periodicity in the image on the surface of the measuring object by a differential processing of the image signals.

A rubbing angle measuring equipment of a structure 4 according to any one of the structures 1 to 3 of the rubbing angle measuring equipment, wherein a relative angle between polarization axes of the polarizer and the analyzer is set to 90°, and the angle formed between the rubbing direction of the measuring object and the polarization axis of the polarizer or the analyzer is set to about 45°.

A rubbing angle measuring equipment of a structure 5 according to any one of the structures 1 to 4 of the rubbing angle measuring equipment, wherein the rubbing angle measuring equipment has means for detecting a mark described in the measuring object or an end of the measuring object, in which the detection means for the mark or the end recognizes, upon measurement of the measuring object, the mark provided to the measuring object or the end thereof, creates a coordinate from the recognized position information with the mark provided to the measuring object or the end thereof as a reference and measures the rubbing angle of the measuring object in the created coordinate.

A rubbing angle measuring equipment of a structure 6 of the invention according to any one of the structures 1 to 4 of the rubbing angle measuring equipment, wherein the rubbing angle measuring equipment has a mark applying function to the measuring object, applies a mark before, after or simultaneously with rubbing angle measurement of the measuring object to the measuring object, creates a coordinate with the applied mark being as a reference, and measures the rubbing angle of the measuring object to the created coordinate.

A rubbing angle measuring equipment of a structure 7 according to any one of the structures 1 to 6 of the rubbing angle measuring equipment, wherein the measuring optical system can move with respect to the measuring object (e.g. move to any position in the measuring object) while keeping the optical arrangement thereof as it is and/or the measuring object can move with respect to the measuring optical system (e.g. move to any position in the measuring optical system), and imaging is possible at arbitrary position (e.g. any position) of the measuring object.

A rubbing angle measuring equipment of a structure 8 according to any one of the structures 1 to 7 of the rubbing angle measuring equipment, wherein a typical point of the measuring object or plural points within a plane thereof are measured, the result of measurement and a standard value are compared to control the rubbing angle.

A rubbing angle measuring equipment of a structure 9 according to any one of the structures 1 to 8 of the rubbing angle measuring equipment, wherein the resolution of the image signal obtained from the imaging means is 512×512 pixels or more.

In a manufacturing method of a liquid crystal device by rubbing at least one of two substrates constituting a liquid crystal cell and sealing liquid crystals between the two substrates of the invention, a process 1 according to the present invention is characterized in that:

a rubbing angle of the substrate is measured by using the rubbing angle measuring equipment according to claim 1 after a step of rubbing the substrate, preferably before bonding together the two substrates.

A process 2 of a manufacturing method of the liquid crystal display device of the invention according to process 1, wherein a branch processing for determining whether the measured rubbing angle falls within a range of control values or not is fed back to the rubbing step to determine rubbing condition therein (in the rubbing step).

A process 3 of a manufacturing method of the liquid crystal display device of the invention according to process 1, wherein the branch processing for determining whether the measured rubbing angle falls within a range of control values or not is fed forward to a process concerning the construction of an optical anisotropic axis after the rubbing step to determine the condition in the process after the rubbing step.

Further, in a manufacturing method of an optical film (birefringence film, etc.) by rubbing the surface of a film (film-like member) and forming a liquid crystal layer (material layer showing birefringence) to the surface), a process 1 according to the present invention is characterized in that:

the rubbing angle of the film is measured by using the rubbing angle measuring equipment according to any one of structures 1 to 7, after a step of rubbing the film. The rubbing angle is measured preferably before forming the aligned crystal layer (birefringence layer) to the film.

A process 2 of a manufacturing method of the optical film of the invention according to the process 1, wherein a branch processing for determining whether the measured rubbing angle falls within a range of control values or not is fed back to the rubbing step to determine the rubbing condition therein (in the rubbing step).

A process 3 of a manufacturing method of the optical film of the invention according to the process 1, wherein a branch processing for determining whether the measured rubbing angle falls within a range of control values or not is fed forward to the cutting process of the film after the rubbing process to determine the condition in the cutting process.

According to the rubbing angle measuring equipment of the invention, by imaging the surface of a substrate or a film after rubbing under Crossed Nichols in a liquid crystal panel or an optical film for which rubbing is conducted in the manufacturing process, rubbing angle thereof can be measured at a high accuracy. Therefore, it is possible to conduct measurement just after rubbing, to feed back the result of the rubbing angle measurement instantly to the rubbing condition or feed forward the result to the condition in the subsequent process such as cutting or overlapping. This enables rubbing at an optimal angle and cutting or overlapping of a base material (film or substrate) conforming the rubbing angle, making it possible to manufacture a liquid crystal panel or the manufacture of an optical film having stable optical characteristics.

BRIEF DESCRIPTION OF THE DRAWINGS

FIG. 1(*a*) and FIG. 1(*b*) are a plan view and a side elevational view of a rubbing angle measuring equipment of a first embodiment according to the present invention;

FIG. 5(*a*) is a schematic view of an imaged obtained by a rubbing angle measuring equipment according to the invention, FIG. 5(*b*) is a schematic view of a power spectrum image obtained by conducting two-dimensional first fourier transforming processing to the image, and FIG. 5(c) is an enlarged view for a central portion of a power spectral image;

FIGS. 6(a) to 6(c) are each a schematic view of an image imaged by a mark detection camera of the rubbing angle measuring equipment;

FIG. 9(a) is a plan view of a rubbing angle measuring equipment described in a third embodiment of the invention, and FIG. 9(b) and FIG. 9(c) are side elevational views thereof;

FIG. 15(a) and FIG. 15(b) are enlarged views each showing a portion of a liquid crystal panel after completion of an overlapping.

DETAILED DESCRIPTION OF THE INVENTION

Figure 2:
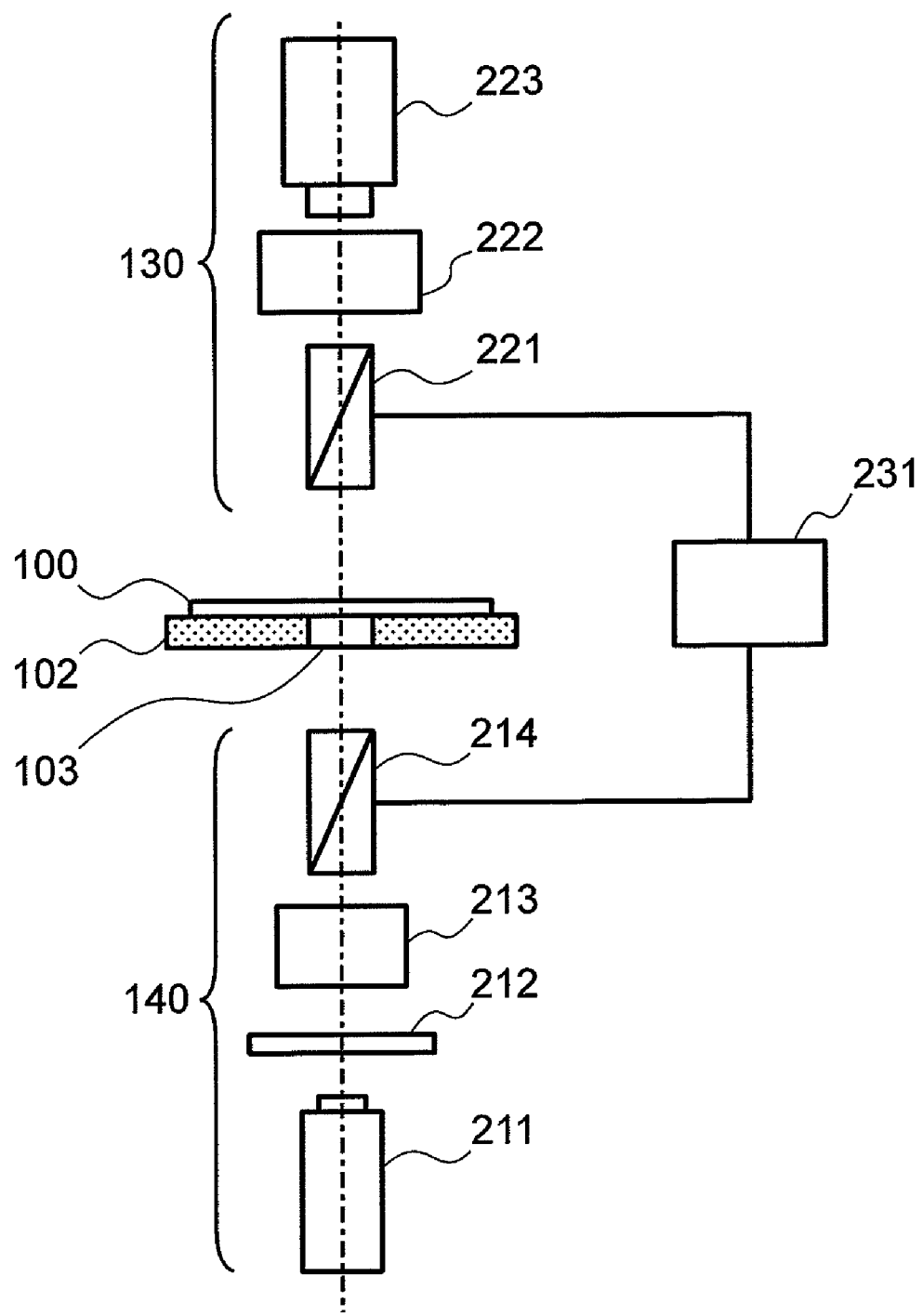
FIG. 2 is a schematic view for an optical system used in the rubbing angle measuring equipment according to the invention.

Preferred embodiments of the present invention are to be described in details with reference to the drawings for preferred embodiments.

EMBODIMENT 1

FIG. 1 shows a rubbing angle measuring equipment according to a first embodiment of the invention. FIG. 1(a) shows a plan view of a rubbing angle measuring equipment according to the embodiment. In the rubbing angle measuring equipment of this embodiment, an imaging unit 130, an imaging unit moving mechanism 111, and an imaging unit moving mechanism support 104 are provided on a surface table 101. The imaging unit 130 has a structure of holding a mark or end detection camera 120 on the lateral side. Further, a stage 102 for holding a measuring object 100 rubbed at the surface for alignment of liquid crystals is provided on a stage moving mechanism 112 (refer to FIG. 1 (b). The stage moving mechanism 112 is provided on the surface table 101. An orthogonal coordinate system shown in FIG. 1(a) is shown, for example, as an X-Y plane within the plane (an upper surface) of the surface table 101.

FIG. 1(b) shows a side elevational view of a rubbing angle measuring equipment of the embodiment. In the rubbing angle measuring equipment of the embodiment, a light source unit 140 is held to a mechanism capable of moving in the direction of axis X in the drawing and moves in synchronization with the imaging unit 130. Accordingly, a light for measurement derived from the light source unit 140 passes a light transmission portion 103 (to be described later with reference to FIG. 2), passes the measuring object 100 and then enters the imaging unit 130. An optical system is constituted such that the surface of the measuring object 100 is focused to the imaging unit. Image signals for the surface of the measuring object obtained by the imaging unit 130 are sent from a signal transmission line 151 to an image evaluation means 150 where image processing is conducted to detect a rubbing angle of the measuring object. Details for the image processing method are to be described later. The orthogonal coordinate system shown in FIG. 1(b) represents the height for the imaging unit 130 relative to the plane of the surface table 101, for example, in the direction of Z axis.

Transmission portions 103 are formed each at a predetermined pitch to the stage 102 on which the measuring object 100 is mounted such that the surface of the measuring object 100 can be imaged at a fixed pitch. In this embodiment, holes are opened for the light transmission portions 103 for transmitting the light but, so long as the characteristic of the transmission light does not change, the constitution of the invention can be changed with no problem even when the light transmission portion 103 is not the hole, and those constituted with a material of small optical anisotropy such as quartz glass can also be used. Further, it may suffice that the light transmission portions 103 are provided so that a desired position for measurement can be observed for the measuring object 100, not being restricted to the fixed pitch. In the rubbing angle equipment of the embodiment, the imaging unit 130 is movable in the direction X and the stage 102 is movable in the direction Y but the mechanism may be structured such that the imaging unit 130 is movable in the direction Y and the stage 102 is movable in the direction X.

Further, it may be constructed such that the imaging unit 130 is movable in the direction X and the direction Y, or the stage 102 is movable in the direction X and the direction Y.

FIG. 2 shows an optical system of the rubbing angle measuring equipment of this embodiment. This is a measuring optical system including a light source unit 140 comprising a light source 211 of a non-polarization light, a filter 212 for controlling the amount of light and wavelength and a polarizer 214 capable of rotation around an optical channel as a center axis, as well as an imaging unit 130 comprising an analyzer 221 capable of rotation around the optical channel as a center axis, an imaging focusing optical system 222 and CCD camera 223 as imaging means, on both side of a stage 102 having a light transmission portion 103. A light from the light source 211 passes the illumination optical system 213, passes the polarizer 214, passes the measuring object 100 rubbed at the surface for aligning liquid crystals, passes the analyzer 221, passes the focusing optical system 222 and is incident to the imaging means 223.

The imaging optical system 222 has a structure capable of exchanging an objective lens and can measure the surface of the measuring object 100 at an optional magnification factor. Further, in the rubbing angle measuring equipment of this embodiment, since the rubbing angle is detected from the image as will be described later, the resolution of the image has an effect on the detection accuracy. Therefore, a CCD area sensor at a resolution of 2048×2048 pixels was used for the CCD camera. Further, a line sensor can also be used for the CCD camera 1223 in which it is necessary to provide the stage 102 with a mechanism moving in synchronization with the reading frequency of the line sensor for imaging the surface of the measuring object. For rubbing angle measurement, it is necessary to set the angle of polarization axis of the polarizer 214 and the analyzer 221 and confirm the attitude of the CCD camera 223. Then, the method is to be described.

A line for recognizing the attitude of the CCD camera 223 as the image forming means relative to the stage is drawn on the stage 102 (not illustrated). This may be any fixed pattern not being restricted to the line and there is no requirement of providing a particular pattern so long as the attitude of the CCD camera is previously known. Further, a mechanism 231 capable of rotating the polarizer 214 and the analyzer 221 while keeping a relative position and capable of rotating the polarizer 214 and the analyzer 221 independently is provided. Further, the angle of the polarization axis of the polarizer 214 and the analyzer 221 to the stage 102 can be set by mounting a calibrating retardation plate such as a ½ wavelength plate with a slow axis angle thereof being known on the stage 102, and measuring the slow axis angle. Further, when one of the polarizer 214 and the analyzer 221 is made detachable, the angle of the polarization axes of the polarizer 214 and the analyzer 221 relative to the stage 102 can be set by measuring the angle of the polarization axis for the calibrating polarizer with the polarization axis angle being known.

Figure 3:
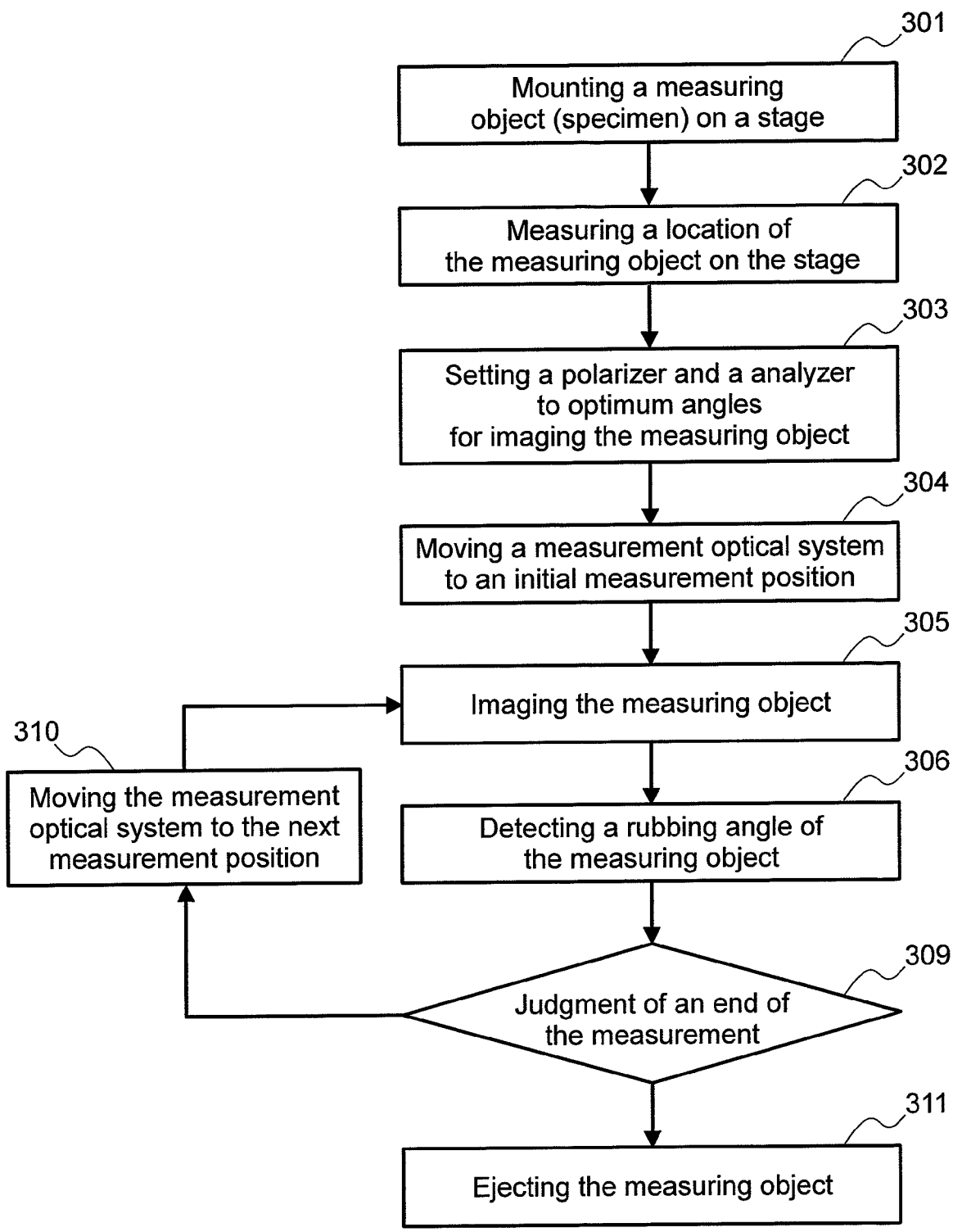
FIG. 3 is a view showing a procedure of measuring a rubbing angle using the rubbing angle measuring equipment according to the invention.

The method of measuring the rubbing angle is to be described. FIG. 3 shows the procedures. At first, a rubbed measuring object is mounted to a stage (step 301). A mark described in the measuring object or an end thereof is detected by a mark or end detection means and the attitude of the measuring object to the stage is measured (step 302). Detailed measuring procedure for the attitude of the measuring object is to be described later. Then, after setting the relative angle between the polarization axes of the polarizer and the analyzer to 90°, the relative position is fixed and set such that the polarization axis of the polarizer is about 45° or −45° to the rubbing direction of the measuring object (step 303). A rough rubbing angle can be judged by the roller angle and the angle of the measuring object upon rubbing. Then, the measuring optical system is moved to an initial measuring position (step 304). The surface of the measuring object is imaged under Crossed Nicols (step 305), image processing such as a two-dimensional fast fourier transformation processing or a differential processing is conducted to the image, signals having an intense periodicity in one direction within the image are detected and the rubbing angle in the measuring object is measured (step 306). Details for the image processing method are to be described later. During image processing, the measuring optical system is moved to the next measuring position (step 310), where the procedures for steps 305, 306, and 309 are repeated to measure the rubbing angle within the plane of the measuring object (for example, X-Y plane in FIG. 1 (a)). When measurement for all measuring set points has been completed, the measuring object is ejected (step 311), to terminate measurement.

A method of detecting the rubbing angle from the imaged image on the surface of the measuring object under Crossed Nicols is to be described. FIG. 5(a) shows a model view of an image on the surface of a measuring object imaged at step 305 in FIG. 3. In FIG. 5(a), optical isotropy given by the rubbing procedure to the surface of the measuring object is observed as fine streaks 501. After controlling the contrast of the image so as to emphasize the streaks, two-dimensional fact fourier transformation processing is conducted to the image, which is converted into a power spectrum shown in the model view of FIG. 5(b). In FIG. 5(b), an intense portion of the signals is indicated black. A line 502 passing the image center is present in a power spectrum image after two-dimensional fast fourier transformation processing. The angle of the line 502 is an angle having an intense periodicity in the original image which is a perpendicular line for the average angle of the streaks 501 in the original image. FIG. 5(c) shows an enlarged view for the central portion of FIG. 5(b). The angle of the line 502 can be determined conveniently by reading the coordinate for the top end 511 in the image from the image center. For example, in FIG. 5(c), assuming the coordinate for the top end 511 of the line as (256, 50) with the center as the original point, the angle a of the line is determined as: a=arctan(50/256)=11.05°. Further, when the coordinate for the top end 511 is displaced upward by one pixel, the coordinate changes to (256, 51) and the angle a of the line is: a=arctan(51/256) =11.27. Accordingly, the measuring resolution power is about 0.2°. As the angle of the line approaches 45°, the measuring resolution power is improved. According to the calibration method, since arctan (256/265)−arctan(255/265)=0.112°, it can be seen that a resolution of at least 512×512 pixels or more is necessary for attaining a measuring resolution power of 0.1° or more.

In the rubbing angle measuring equipment of this embodiment, the angle of the line 502 is detected by using Hough transformation. Since it has been known that the line to determine the angle passes the original point in this measurement, when the power spectrum image after two-dimensional fast fourier transformation processing is on a $w_x w_y$ plane and polar coordinate transformation is conducted from $w_y = aw_x + b$ to $\rho = w_x \sin \theta + w_y \cos \theta$, since premise: b=0 is always established and it can be set as: $\rho = 0$, calculation is possible in an actual processing time. Further, weighing for the signal intensity and elimination of low frequency component (black block near the original point) are conducted, to enhance the accuracy for the angle detection thereby enabling measurement for the rubbing angle at an accuracy of 0.05° or higher.

Further, in a case of determining the streak angle, there is also a method of not conducting the two-dimensional fast fourier transformation processing. This is a method of determining the angle of conducting the differential processing on an original image on the premise that the line to determine the angle passes the original point in the $w_x w_y$ plane. This is shown below. Periodically fluctuating signals on the original image are represented by equation 1 (A: signal amplitude, $W_x$: frequency in the direction x, $W_y$: frequency in the direction y, a: gradient).

$$f(x,y) = A \cos(W_x x + W_y y) \tag{Equation 1}$$

Since the line passes the original point on the spectrum image, a relation: $W_y = aW_x$ is established, so that equation (1) is rewritten as equation (2).

$$f(x, y) = A \cos(W_x x + aW_x y) \tag{Equation 2}$$

The equation 2 is put to partial differentiation with x, y respectively into equation 3 and equation 4.

$$df/dx = -AW_x \sin(W_x x + aW_x y) \tag{Equation 3}$$

$$df/dy = -AaW_x \sin(W_x x + aW_x y) \tag{Equation 4}$$

A gradient a is determined by (equation 4)/(equation 3). The perpendicular line at the gradient a is a rubbing angle. Also in this case, more accurate angle detection can be conducted by conducting weighting for the signal intensity and elimination of low frequency components. In addition, any algorithm capable of detecting signals having an intense periodicity in the original image can be used for the apparatus of the invention. As described above, since signals having intense periodicity in the original image are detected, angle can be detected with no problems even when defects of films or obstacles are present in the observation region if they are minute.

In the image processing method described above, since the rubbing angle in the image is detected, in a case where the measuring object is slanted to the stage, the image to be taken is also slanted and error due to the slanting is caused to the result of measurement for the rubbing angle. Accordingly, for accurate angle measurement, it is important to measure the accurate attitude of the measuring object to the stage. Then, a method of measuring the attitude of the measuring object to a stage by using a mark described in the measuring object is to be described. Marks at three positions arranged in a row described in the measuring object are taken up by a mark detection camera. FIG. 6(a) to FIG. 6(c) show model views of the obtained image of mark. Hatched portion 602, 612, and 613 each represents a mark in the image (for example, alignment mark formed to the measuring object). While FIG. 6(a) shows an x coordinate 601 and a y coordinate 603 passing the gravitational center of the mark 602 but such indications are not illustrated in FIG. 6(b) and FIG. 6(c).

For each of the marks shown in FIG. 6(a) to FIG. 6(c), a mark shape is recognized and barycentric coordinates ($\Delta x_a$, $\Delta y_a$), ($\Delta x_b$, $\Delta y_b$), ($\Delta x_c$, $\Delta y_c$) for respective marks in the image are detected. Assuming the original coordinates for the respective images to the stage as ($x_a$, $y_a$), ($x_b$, $y_b$), ($x_c$, $y_c$), respectively, the barycentric coordinates for the respective marks to the stage are ($x_a+\Delta x_a$, $y_a+\Delta y_a$), ($x_b+\Delta x_b$, $y_b+\Delta y_b$), ($x_c+\Delta x_c$, $y_c+\Delta y_c$), respectively. Linear approximation is conducts on the barycentric coordinates for respective marks to the three stages and the attitude of the measuring object to the stage is detected. The information for the attitude of the measuring object is reflected on the result of measurement for the rubbing angle. While the attitude of the measuring object was measured from the marks at three positions in this embodiment, the attitude of the measuring object can be measured without using plural marks. That is, it may suffice to describe mark(s) at one or more positions capable of measuring the attitude of the measuring object may be described on the measuring object. In a case of describing plural marks in the plane of the measuring object, the attitude of the measuring object can be measured more accurately by detecting marks spaced apart from each other in the plane. Further, instead of the mark, other markers such as the end of the measuring object may also be used for the measurement of the attitude of the measuring object.

EXAMPLE 2

Figure 7:
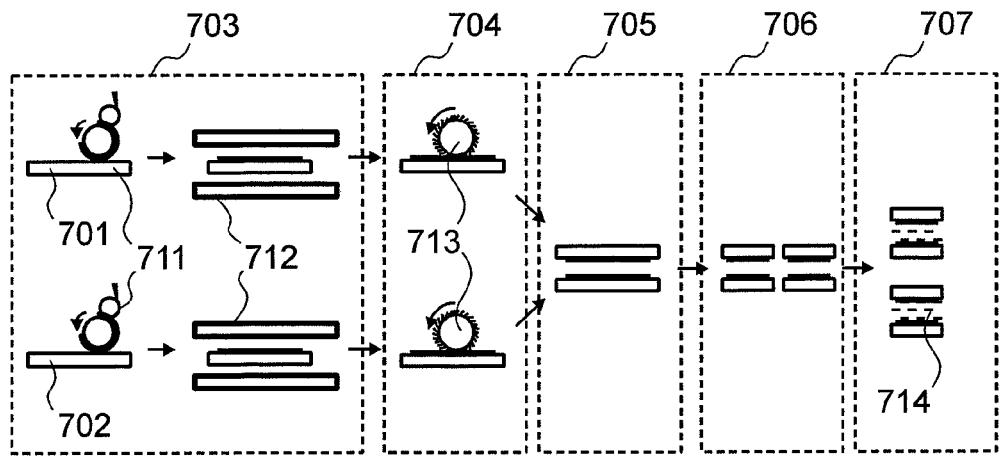
FIG. 7 is a schematic view of a liquid crystal panel manufacturing process according to the invention.
Figure 13:
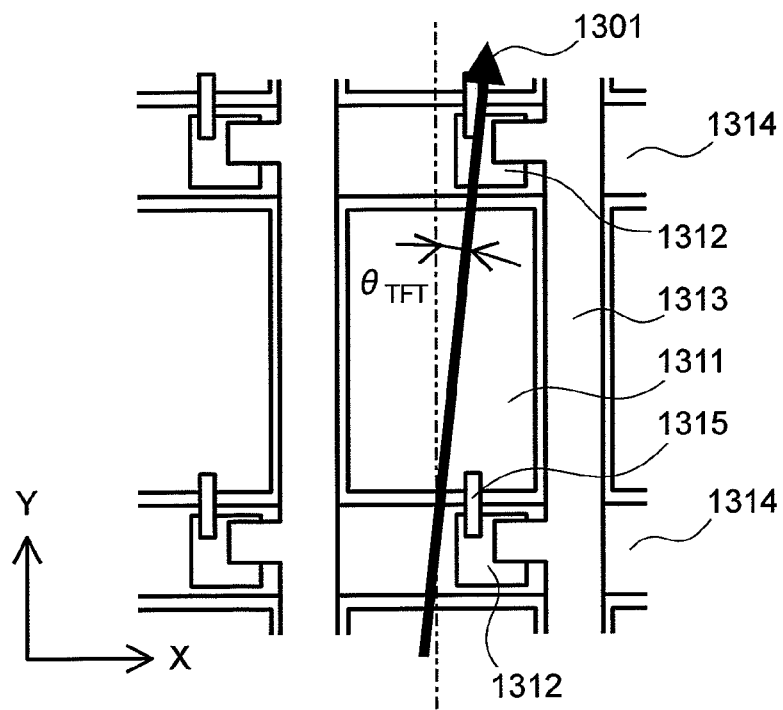
FIG. 13 is an enlarged view for a portion of a TFT substrate (one pixel and vicinity thereof)
Figure 14:
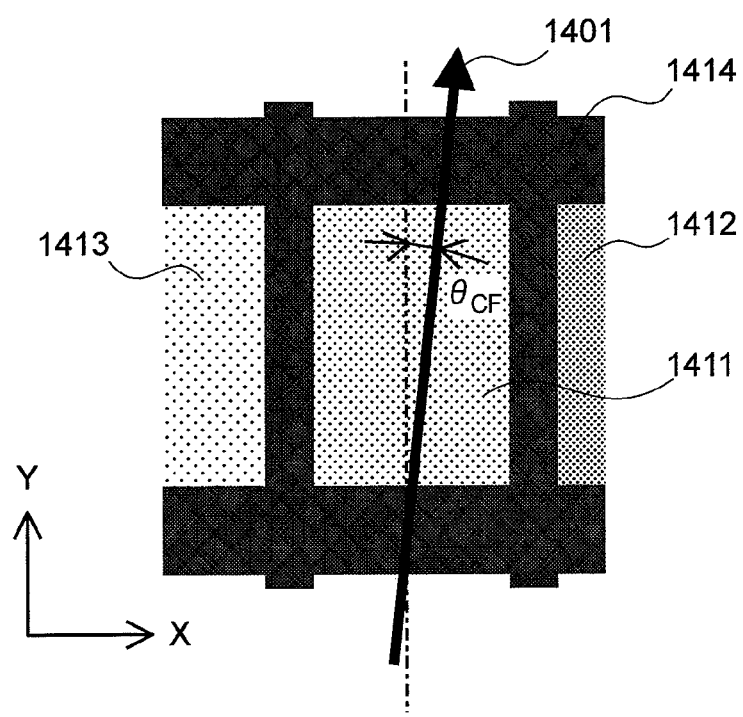
FIG. 14 is an enlarged view for a portion of a CF substrate.

FIG. 7 shows an example of a manufacturing process for a liquid crystal panel. The manufacturing process for the liquid crystal panel includes an alignment film forming process 703 of coating a polymeric solution such as of a polyimide to a CF substrate 701 and a TFT substrate 702 by a flexographic printing press 711 and calcining in a calcination furnace 712, a rubbing process 704 of rotating a rubbing roller 713 which is wound around with a rubbing cloth at a high speed to rub the surface of an alignment film to apply anchoring energy to respective substrates, an overlapping step 705 of opposing and overlapping the processed surfaces of the CF substrate 701 and the TFT substrate 702 such that the rubbing directions are in inverse parallel, a cutting step 706 of dividing the same into a multi-facetted panel size, and a liquid crystal sealing process 707 of sealing liquid crystals 714. While the CF substrate 701 and the TFT substrate 702 were used, a glass substrate not provided with a circuit or a color filter may also be used for either one or both of them. The TFT circuit is constituted as a pixel described, for example, with reference to FIG. 13, and the color filter is constituted as described, for example, with reference to FIG. 14. The manufacturing processes described above are one example, and there are also other methods, for example, a method of using an ink jet coating machine instead of the flexographic printing press or a method of dripping liquid crystals before overlapping of substrates.

Figure 4:
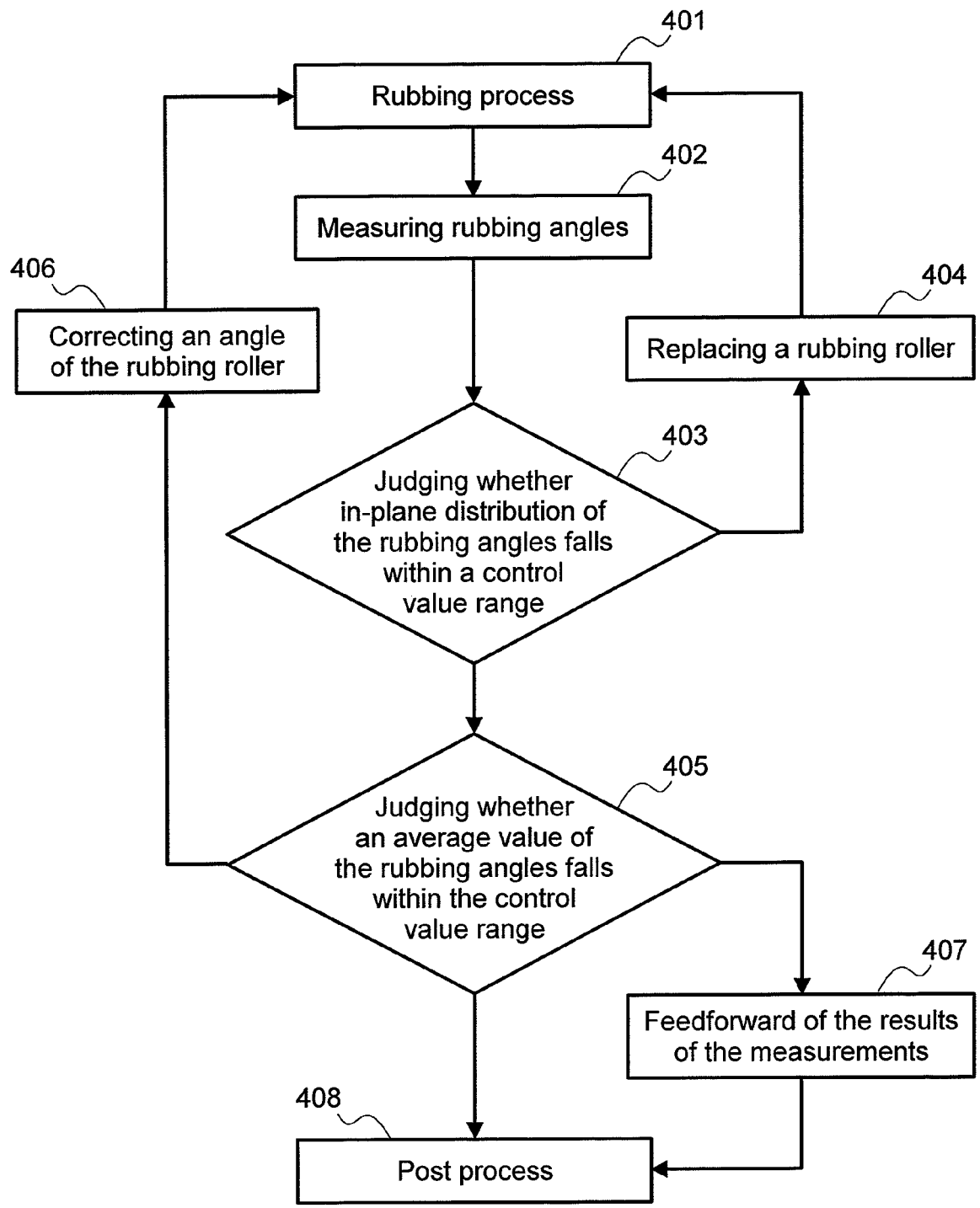
FIG. 4 is a view showing an aligned angle control procedure using the rubbing angle measuring equipment according to the invention.

An example of conducting control for the rubbing process in the manufacturing process of the liquid crystal panel by using the rubbing angle measuring equipment shown in Embodiment 1 between the rubbing process 704 and the overlaying process 705 in FIG. 7 is to be described with reference to FIG. 4. At first, rubbing is applied to the substrate (step 401) and a rubbing angle in a substrate plane is measured by using the rubbing angle measuring equipment described in Embodiment 1 (step 402). It is judged whether the thus measured in-plane distribution of the rubbing angles falls within a range of control value ranges (step 403). As a result of the judgment, when this is out of the range of the control values, the rubbing roller is replaced (step 404), and the procedure is conducted again from the step 401. The procedure of the step 404 is not restricted to the replacement of the rubbing roller but feedback may be conducted to a method capable of improving the in-plane distribution of the rubbing angle. In a case where the in-plane distribution of the rubbing angles falls within the range of control values, it is then judged whether an in-plane average value of the rubbing angle falls within the range of control values or not (step 405). As a result of the judgment, in a case where this is out of the range of control values, the angle of the rubbing roller is corrected (step 406) and the procedure is conducted again from step 401. In the step 406, it may be fed back to means capable of changing the average rubbing angle in the plane of the substrate such as correction for the rotational angle of the substrate before rubbing.

In a case where the average value of the rubbing angles measured in the plane of the substrate falls within the range of control values, the substrate is delivered to the post process (step 408). Even in a case where the rubbing angle is out of the control value range in the steps 403, 405, the liquid crystal panel can be manufactured also by feeding forward the result of measurement in the step 402 to the post-process concerning the construction of the optical anisotropic axis such as cutting, substrate overlapping or appending of an optical film while correcting the angle of the optical anisotropic axis. While measurement for the rubbing angles was conducted at plural positions in the plane of the substrate, a simple and convenient control is possible also by measuring only one typical point in the plane. The control method for rubbing shown in FIG. 4 can be carried out as a check of the rubbing condition before mass production, or can be carried out for the substrates in the mass production as 100% measurement for sampled measurement.

Figure 8:
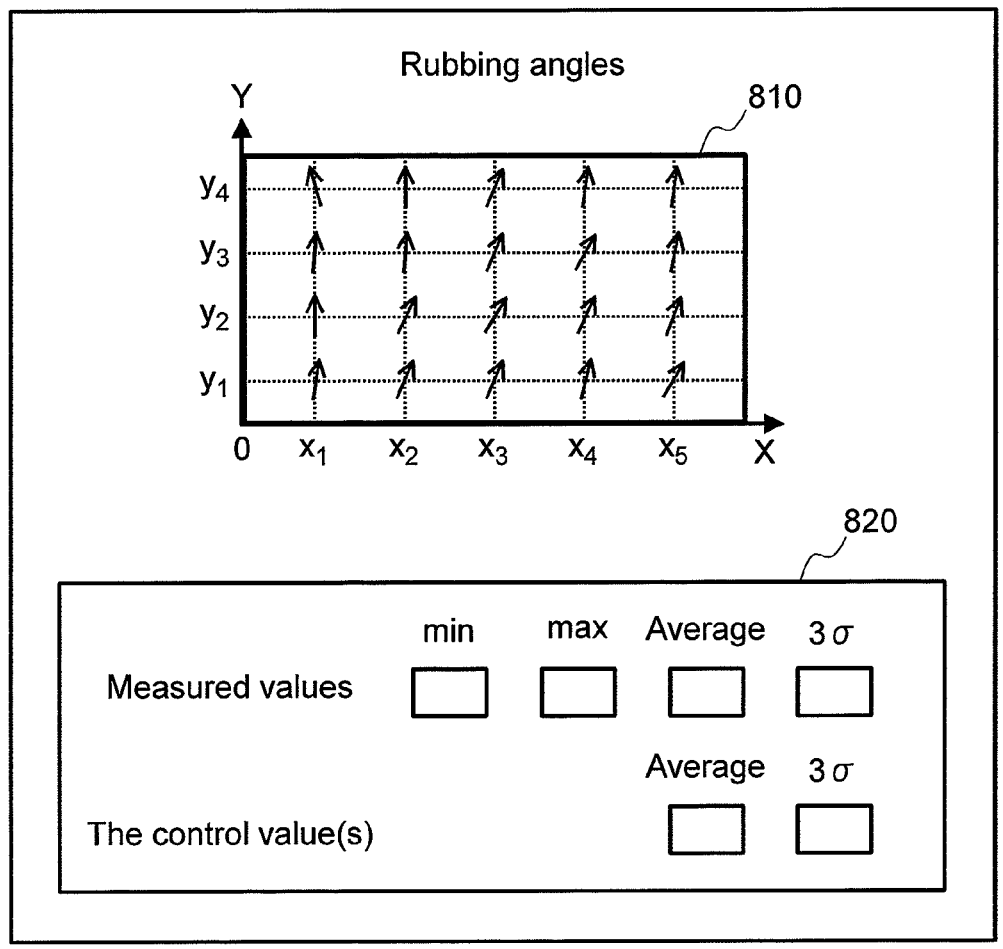
FIG. 8 is a view showing a user interface of the rubbing angle measuring equipment according to the invention.

FIG. 8 shows an example of a user interface displaying the measuring result of rubbing angles in the substrate plane. A rubbing angle at each measuring position in the plane of the substrate is indicated by an arrow (screen 810). Further, control values and measured values for the in-plane distribution and the average value in the rubbing direction are indicated (screen 820). Further, by measuring and controlling the information on every substrates or every lots, optical characteristics upon completion of a panel can be predicted.

EMBODIMENT 3

FIG. 9 shows an outline of a rubbing angle measuring equipment as a third embodiment of the invention. FIG. 9(a) is an X-Y plane view of a rubbing angle measuring equipment according to the invention, FIG. 9(b) is an XZ plan view and FIG. 9(c) is a YZ plan view. The rubbing angle measuring equipment of this embodiment is designed for an elongate measuring matter such as an optical film as an object. The equipment includes a light source unit 901, an illumination optical unit support 910, an imaging unit 903, a laser irradiation unit 907, a signal transmission line 904, and an image evaluation means 906. A line sensor at high sensitivity is used for the imaging means of the imaging unit 903 and the imaging means operates at a frequency in synchronization with a winding speed of an elongate measuring object 902 to obtain an image on the surface of the measuring object 902. A measuring light derived from the light source unit 901 passes the measuring object 902 and enters the imaging unit 903. The image information on the surface of the measuring object obtained by the imaging unit 903 is transmitted from the signal transmission line 904 to the image evaluation means 906 and put to image processing by the image evaluation means 906 and the rubbing angle is detected. The detection method has been described in Embodiment 1. Further, the laser irradiation unit 907 has an ability of providing a mark to the measuring object, the attitude and the position of the imaging unit 903 to the applied mark are known and the relative position thereof is fixed. The image evaluation means 906 outputs a rubbing angle to the coordinate with a mark being as a reference. In a case where the application of the mark is not necessary, laser irradiation unit 907 can use the mark or the end detection means described in Embodiment 1 inspected. The optical system for the rubbing angle measuring equipment of this embodiment is identical with the optical system of the rubbing angle measuring equipment of the first embodiment excepting that the stage is not present and this is constituted as shown in FIG. 2. Detailed descriptions for the optical system are as described in Embodiment 1.

EMBODIMENT 4

Figure 10:
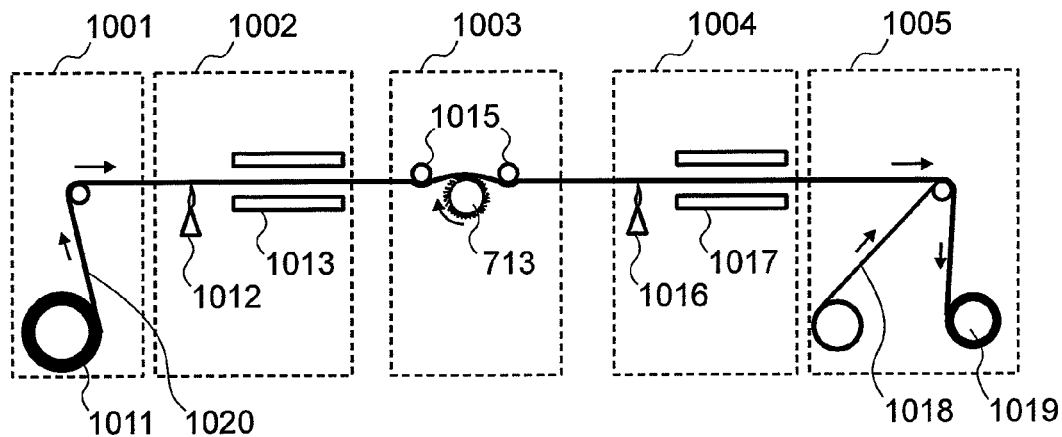
FIG. 10 is a schematic view of an optical film manufacturing process according to the invention.

FIG. 10 shows a model view of a manufacturing method of an optical film prepared by rubbing a film surface and forming a liquid crystal layer (birefringence material layer) on the surface. The optical film manufacturing process includes an alignment film forming process 1002 of coating a polymeric solution to a transparent film 1020 supplied from supplying means 1001 of an elongate film by an applicator 1012, and calcining the same in a furnace 1013, a rubbing step 1003 of the rubbing the surface of an aligned film by a rubbing roller 713, a liquid crystal layer forming process 1004 of coating liquid crystals (liquid crystal polymer) to the film after rubbing by a coating machine 1016 thereby forming a liquid crystal layer, and a surface protection process 1005 for protecting the surface with a protection film 1018. An elongate film is mounted, for example, as a roll 1011 of a base film to the supply means 1001. In the rubbing process 1003, the intensity of rubbing the film with the rubbing roller 713 is controlled by a pinch roller 1015. The film covered at the surface formed of the liquid crystal layer with the protection film 1018 (optical film in a completed state) in the surface protection process 1005 is wound into a take-up roll 1019 in an elongate state as it is.

Figure 11:
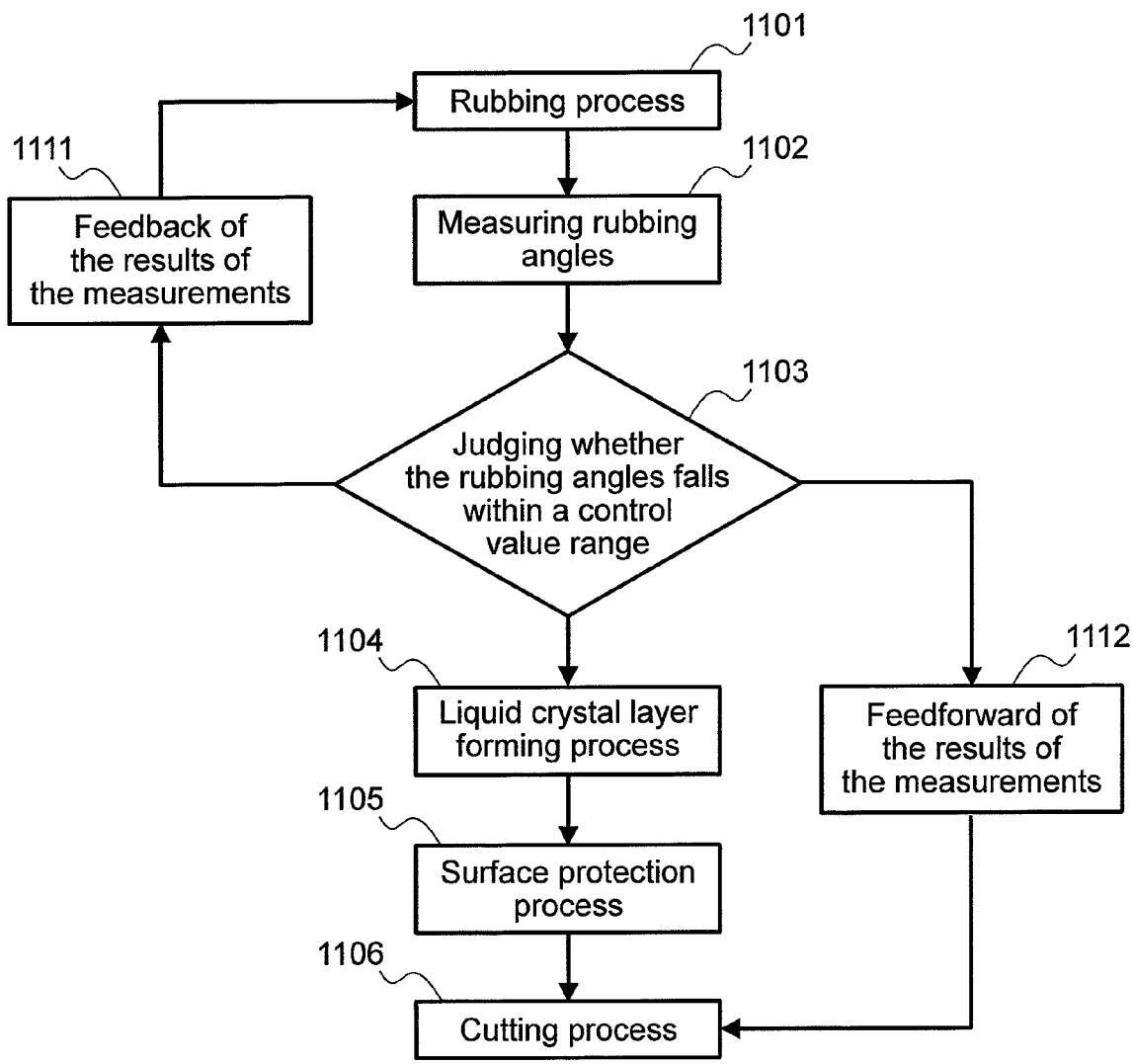
FIG. 11 is a view showing an aligned angle control procedure for an elongate film using the rubbing angle measuring equipment according to the invention.
Figure 12:
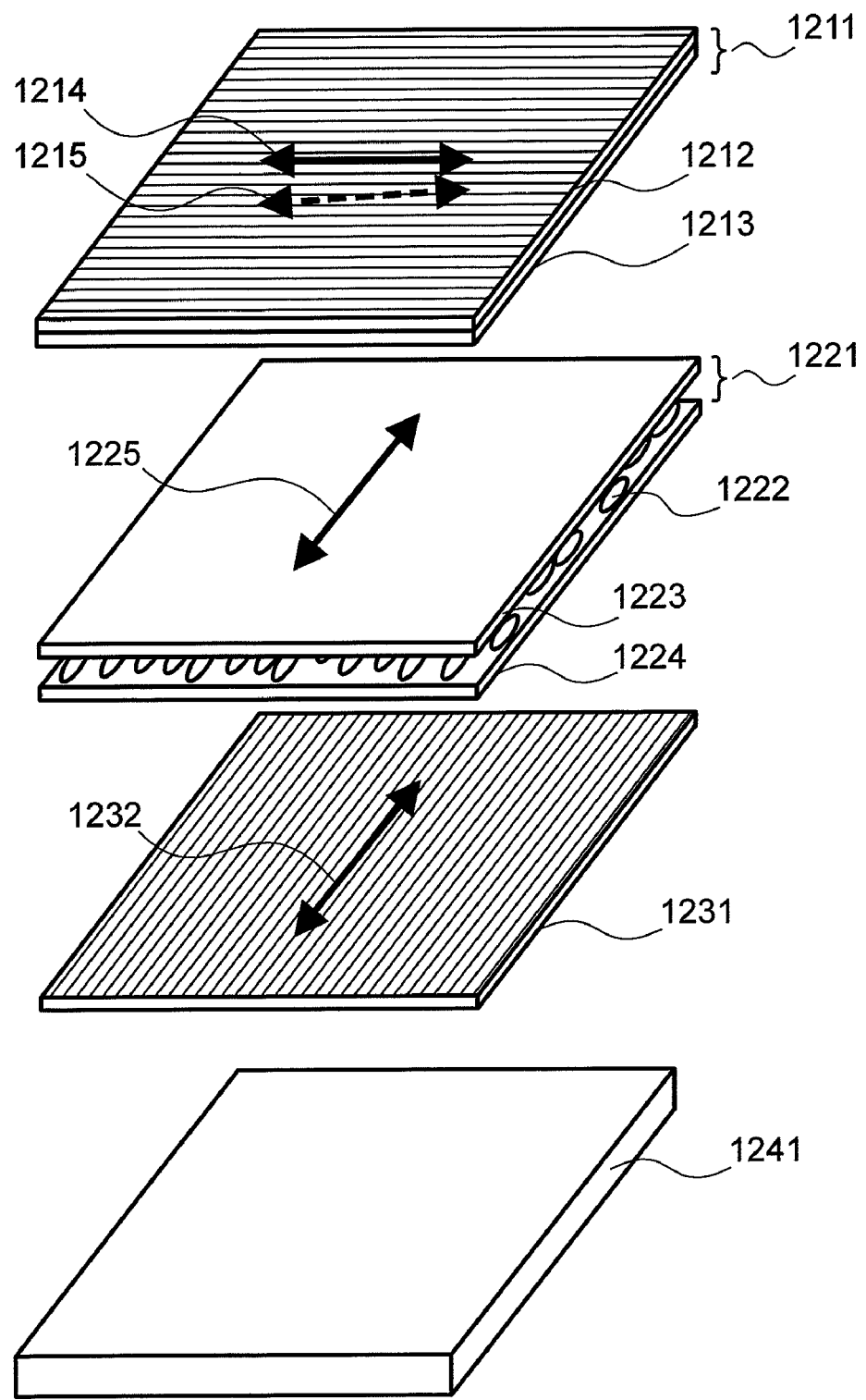
FIG. 12 is a schematic view showing an optical anisotropic axis constituting an IPS system liquid crystal display.

An example of conducting control for rubbing in the manufacturing process of the optical film by using the rubbing angle measuring equipment shown in Embodiment 3 between the rubbing process 1003 and the liquid crystal layer forming process 1004 of FIG. 10 shown in Embodiment 3 is to be described with reference to FIG. 11. Rubbing is applied to the film (step 1101) and the rubbing angle of the film rubbed by the method described in Embodiment 3 is measured (step 1102). It is judged whether the rubbing angle of the film falls within a range of control values or not (step 1103). As a result of judgment, in a case where it is out of the range of control values, this is fed back to the rubbing process where rubbing roller is exchanged or the roller angle is changed (step 1111). The information of the rubbing angle is transferred to the cutting step and reflected to the cutting angle (step 1112). The film out of the range of control values is cut at an optimal angle for the rubbing angle (step 1106).

INDUSTRIAL APPLICABILITY

According to the rubbing angle measuring equipment of the invention described above, the rubbing angle of the rubbed measuring object can be measured a non-destructive manner, within a short time, and at a high accuracy. In the manufacturing process of the liquid crystal panel and the optical film for conducting rubbing, since the result of measurement for the rubbing angle just after rubbing can be reflected to each of the processes concerning the construction of the optical anisotropic axis and the condition for each of the processes can be corrected, this can contributed to the improvement of the optical performance of the liquid crystal panel and the optical film.

Further, since the rubbing angle of the TFT substrate and the CF substrate of the liquid crystal panel and the optical film can be measured, the optical performance upon completion of the liquid crystal panel formed by overlapping the TFT substrate and the CF substrate can be predicted and, further, the optical performance upon bonding the optical film to the liquid crystal panel can be predicted. Further, since it can be applied as a control method of the optical axis angle upon preparing the function of the retardation plate or the polarization plate to the substrate per se of the liquid crystal panel, it can contribute to the improvement of the image quality of the liquid crystal display.

While we have shown and described several embodiments in accordance with the present invention, it is understood that the same is not limited thereto but is susceptible of numerous changes and modifications as known to those skilled in the art, and we therefore do not wish to be limited to the details shown and described herein but intend to cover all such changes and modifications as are encompassed by the scope of the appended claims.

What is claimed is:

1. A rubbing angle measuring equipment including
a light source unit, a measuring optical system, an imaging means, and an image evaluation means, wherein:
the light source unit is constituted such that a light from a light source is illuminated through an illumination optical system and a polarizer to a surface-rubbed measuring object;
the measuring optical system is constituted such that the light transmitting the measuring object is entered through an analyzer and a focusing optical system to the imaging means and focused on the surface of the measuring object; and
the image evaluation means receives image signals obtained by the imaging means, detects signals having an intense periodicity in the image and measures the rubbing angle of the measuring object.

2. The rubbing angle measuring equipment according to claim 1, wherein the image evaluation means detects signals having the intense periodicity in the image on the surface of the measuring object by a two-dimensional fast fourier transforming processing of the image signals.

3. The rubbing angle measuring equipment according to claim 1, wherein the image evaluation means detects the signals having the intense periodicity in the image on the surface of the measuring object by a differential processing of the image signals.

4. The rubbing angle measuring equipment according to claim 1, wherein a relative angle between polarization axes of the polarizer and the analyzer is set to 90°, and the angle formed between the rubbing direction of the measuring object and the polarization axis of the polarizer or the analyzer is set to about 45°.

5. The rubbing angle measuring equipment according to claim 1, wherein:

the rubbing angle measuring equipment has means for detecting a mark described in the measuring object or an end of the measuring object;

the detection means for the mark or the end recognizes, upon measurement of the measuring object, the mark provided to the measuring object or the end thereof, creates a coordinate from the recognized position information with the mark provided to the measuring object or the end thereof as a reference and measures the rubbing angle of the measuring object in the created coordinate.

6. The rubbing angle measuring equipment according to claim 1, wherein the rubbing angle measuring equipment has a mark applying function to the measuring object, applies a mark before, after or simultaneously with rubbing angle measurement of the measuring object to the measuring object, creates a coordinate with the applied mark being as a reference, and measures the rubbing angle of the measuring object to the created coordinate.

7. The rubbing angle measuring equipment according to claim 1, wherein the measuring optical system can move with respect to the measuring object while keeping the optical arrangement thereof as it is and/or the measuring object can move with respect to the measuring optical system, and imaging is possible at arbitrary position of the measuring object.

8. The rubbing angle measuring equipment according to claim 1, wherein a typical point of the measuring object or plural points within a plane thereof are measured, the result of measurement and a standard value are compared to control the rubbing angle.

9. The rubbing angle measuring equipment according to claim 1, wherein the resolution of the image signal obtained from the imaging means is 512×512 pixels or more.

10. A manufacturing method of a liquid crystal device of rubbing at least one of two substrates constituting a liquid crystal cell and sealing liquid crystals between the two substrates, wherein a rubbing angle of the substrate is measured by using the rubbing angle measuring equipment according to claim 1 after a step of rubbing the substrate.

11. The manufacturing method of a liquid crystal display device according to claim 10, wherein a branch processing for determining whether the measured rubbing angle falls within a range of control values or not is fed back to the rubbing step to determine rubbing condition therein.

12. The manufacturing method of a liquid crystal display device according to claim 10, wherein the branch processing for determining whether the measured rubbing angle falls within a range of control values or not is fed forward to a process concerning the construction of an optical anisotropic axis after the rubbing step to determine the condition in the process after the rubbing step.

13. A manufacturing method of an optical film of rubbing the surface of the film and forming a liquid crystal layer to the surface, wherein:

the rubbing angle of the film is measured by using the rubbing angle measuring equipment according to claim 1, after a step of rubbing the film.

14. The manufacturing method of an optical film according to claim 13, wherein a branch processing for determining whether the measured rubbing angle falls within a range of control values or not is fed back to the rubbing step to determine the rubbing condition therein.

15. The manufacturing method of an optical film according to claim 13, wherein a branch processing for determining whether the measured rubbing angle falls within a range of control values or not is fed forward to the cutting process of the film after the rubbing process to determine the condition in the cutting process.

* * * * *